United States Patent [19]

Vlahakis et al.

[11] Patent Number: 5,419,879
[45] Date of Patent: May 30, 1995

[54] PERFUMED STABLE GEL COMPOSITION

[75] Inventors: Eftichios V. Vlahakis, 16727 Bolero La., Huntington Beach, Calif. 92649; John A. Manolas, Lake Forest; Michael J. Marrese, Park Ridge, both of Ill.

[73] Assignee: Eftichios Van Vlahakis, Huntington Beach, Calif.

[21] Appl. No.: 184,975

[22] Filed: Jan. 21, 1994

Related U.S. Application Data

[63] Continuation-in-part of Ser. No. 970,122, Nov. 2, 1992.

[51] Int. Cl.⁶ .......................... A61L 9/01; A61L 9/04; B01J 7/00; A61K 7/46
[52] U.S. Cl. ........................................ 422/305; 422/5; 424/76.4; 514/944; 512/2
[58] Field of Search ................... 422/4, 5, 305; 424/76.2, 76.3, 76.4, 76.1, 400; 512/2, 1, 3; 514/944

[56] References Cited

U.S. PATENT DOCUMENTS

| | | | |
|---|---|---|---|
| 4,067,824 | 1/1978 | Teng et al. | 514/4 |
| 4,117,110 | 9/1978 | Hautmann | 424/76.3 |
| 4,137,196 | 1/1979 | Sakurai et al. | 512/2 |
| 4,178,264 | 12/1979 | Streit et al. | 424/76.3 X |
| 4,755,377 | 7/1988 | Steer | 424/76.4 |
| 5,021,066 | 6/1991 | Aeby et al. | 8/408 |
| 5,034,222 | 7/1991 | Kellett et al. | 424/76.4 |
| 5,039,513 | 8/1991 | Chatterjee et al. | 424/47 |
| 5,047,234 | 9/1991 | Dickerson et al. | 424/76.3 X |
| 5,060,858 | 10/1991 | Santini | 239/60 |

*Primary Examiner*—Robert J. Warden
*Assistant Examiner*—E. Leigh Dawson
*Attorney, Agent, or Firm*—Wallenstein & Wagner, Ltd.

[57] ABSTRACT

The present invention relates to a perfumed stable gel comprised of a unique combination of a chemical components. The stable gel can be maintained at temperatures of from about 125° F. to about 150° F. and has a perfume content of from about 70.0% to about 85.0% by weight of the composition. The perfumed stable gel also comprises a surfactant, a soap, an odorless glycol, water, a preservative and optional components, such as dyes, inert filler materials, and ethanol or odorless mineral spirits. The perfumed stable gel may be retained in a disposable deodorant container which is adapted for use with various deodorant dispensers.

33 Claims, 7 Drawing Sheets

——— NET WEIGHT

── NET WEIGHT

PERFUMED STABLE GEL COMPOSITION

RELATED APPLICATION

The present application is a continuation-in-part of U.S. application Ser. No. 07/970,122, filed on Nov. 2, 1992, to issue as a U.S. Patent.

DESCRIPTION

Technical Field

The present invention relates to a perfumed stable gel comprised of a unique combination of chemical components. The stable gel can be maintained at temperatures of from about 125° F. to about 150° F. and has a perfume content of from about 70.0% to about 85.0% by weight of the composition. The perfumed stable gel also comprises a surfactant, a soap, an odorless glycol, water, a preservative and optional components, such as dyes, inert filler materials, and ethanol or odorless mineral spirits. The perfumed stable gel may be retained in a disposable deodorant container which is adapted for use with various deodorant dispensers.

BACKGROUND PRIOR ART

Deodorant containers holding an evaporative perfumed gel type deodorant for freshening the air of restrooms of commercial establishments are well known in the field of deodorizing and air freshening agents. The controlled dispensing of fragrance and the capacity to create an odor impression in a substantially closed space are concerns which are continually addressed in the field of deodorizing and air freshening agents. The importance of a controlled release or evaporation rate is important in determining the amount of fragrance to be used in the air freshening agent and in determining the functional life of the unit itself.

Solid compositions in which a fragrance or perfume is added to gelling agents offer a desirable and relatively low cost commercial delivery method for continuous action fragrance release devices. A method and apparatus for dispensing volatile components of an air treating gel is disclosed in U.S. Pat. No. 5,060,858 to Santini. In addition, a composite gel-foam air freshener is disclosed in U.S. Pat. No. 5,034,222 to Kellett et al.

Prior art patents relating to perfumed gel compositions include U.S. Pat. No. 4,755,377 to Steer for a foamed air freshener composition, U.S. Pat. No. 4,137,196 to Sakurai et al. for a gelatinous fragrance-imparting composition containing stabilized perfume, and U.S. Pat. No. 4,067,824 to Teng et al. for a gelled perfume formulation.

Disadvantages of known gel-based air fresheners include rapid evaporation rates of the gel compositions, temperature instability, and inefficiency of perfume release wherein the perfume components are not released into the air but become entrapped in the gel residue. Disadvantages such as lack of temperature and heat stability can result in product evaporation, deterioration of product appearance, and loss of deodorizing effectiveness. Therefore, a need exists for a perfumed gel deodorizer which is long-lasting, stable at high temperatures, and able to sustain an effective release rate of fragrance from the perfumed stable gel in both normal and adverse conditions.

In addition, the containers used to retain and dispense the perfumed gel compositions are known in the prior art. An open topped container having a perforated decorative cover and used for the dispensation of volatile components of a gel is disclosed in U.S. Pat. No. 5,060,858 to Santini. Other containers typically used to retain deodorizing agents include aluminum cups having an aluminum lid with a pull-back tab and open top containers covered by a layer of porous material.

The present invention is an improvement over the prior art in that none of the prior art inventions disclose a deodorant dispenser containing a chemical composition in the form of a perfumed stable gel, wherein the perfumed stable gel can be maintained at high temperatures and has a perfume content of from about 70.0% to about 85.0% by weight of the composition. In addition, none of the prior art inventions disclose a container having a base with a top surface and a bottom surface and having intersecting diametrical grooves on the bottom surface and four equi-angularly spaced support ribs or fins on the top surface which extend radially inwardly from the peripheral wall.

Previously, it was difficult to manufacture a product that could be maintained as a stable gel when exposed to temperatures of from about 125° F. to about 150° F., when that product also included a perfume content of from about 70.0% to about 85.0% by weight of the composition. Obtaining a stable gel with a perfume content of from about 70.0% to about 85.0% has also been difficult to develop from a solubility perspective, as most other gels will liquefy, even at room temperatures, at levels of 50% perfume content. Up until now, there was no known perfumed stable gel with a melting point of from about 125° F. to about 150° F. and having a perfume content of from about 70.0% to about 85.0% by weight of the composition. Thus, the need persisted for an easily manufactured, durable deodorant container holding a long-lasting and effective perfumed stable gel having a perfume content of from about 70.0% to about 85.0% by weight of the composition and maintaining its stability at high temperatures without undue evaporation.

In addition, because the gel has a high perfume content, it is a characteristic of the gel for its perfume components to evaporate over time. Thus, the perfumed stable gel is typically provided in a replaceable container so that it can be easily replaced when it has evaporated. The deodorant containers are typically shaped into a unique form corresponding to the shape of their respective dispensers. This greatly limits the interchangability of such replacement containers. Thus, it is desired to provide a gel container that can be adapted to and that can be placed into a broad range of dispensers. The dispensers that are used with the deodorant containers of the present invention may include a means for drawing air across the perfumed stable gel, for example, in the form of battery operated fan dispenser units. The dispensers may also be in the form of stand alone units. Typically, the deodorant containers filled with the perfumed stable gels can be used in conjunction with dispensers manufactured by the following: (1) F-Matic, (2) Impact, (3) Georgia Pacific, and (4) Technical Concepts. However, the container retaining the perfumed stable gel composition of the present invention is not limited to use with the aforementioned dispensers.

It is also a characteristic of air freshening gels to shrink and harden as the perfume components of the gels evaporate. As the gel shrinks, the surface area is reduced, and the rate of perfume escape is decreased. Thus, it is desired to provide a deodorant container which limits or decreases gel shrinkage and hardening.

Finally, when the deodorant container and gel are shipped, they are subjected to shaking and otherwise generally rough handling. It is desired to provide a deodorant container which securely supports the gel during shipping and which is tough and rigid in structure.

SUMMARY OF THE INVENTION

The present invention relates to a perfumed stable gel comprised of a unique combination of chemical components. The perfumed stable gel may be retained in and dispensable from a disposable container assembly which is adapted for use with various deodorant dispensers.

In a principal embodiment, the deodorant container itself comprises a shell structure, preferably cylindrical in shape and having a peripheral wall, a base and an open top. The base includes a top surface and a bottom surface. The base further includes a pair of intersecting diametrical grooves on the bottom surface and four equi-angularly spaced support ribs on the top surface which extend radially inwardly from the peripheral wall. Each of the ribs terminate with a perpendicular end portion closest to the center of the deodorant container. The intersecting diametrical grooves form corresponding intersecting diametrical ridges on the top surface of the base, and the ribs extend upwardly from the ridges. The peripheral wall terminates with a radially outwardly extending lip.

The disposable deodorant container retains a perfumed stable gel which is comprised of a unique combination of chemical components. The perfumed stable gel can be maintained as a gel when exposed to temperatures of from about 1.25° F. to about 150° F. and has a perfume content of from about 70.0% to about 85.0% by weight of the composition. The perfumed stable gel comprises the following components: a surfactant, a soap, an odorless glycol, a perfume, water, a preservative and optional components, such as dyes, inert filler materials, and ethanol or odorless mineral spirits. The deodorant container and improved perfumed stable gel composition may be simply and economically manufactured in a unitary assembly by pouring the perfumed stable gel chemical composition while in a fluid state into the protective shell of the deodorant container and allowing the perfumed gel to set. The container is then heat-sealed with a foil top covering. The foil top covering may be removed from the deodorant container when the deodorant container is placed in a dispenser for use in deodorizing a room or area.

The deodorant containers can be utilized with various dispensers and particularly with those dispensers installed in restrooms of commercial establishments. Such dispensers used in conjunction with the deodorant container of the present invention may include a means for drawing air across the perfumed stable gel, for example, in the form of battery operated fan dispenser units. The dispensers used in conjunction with the deodorant container of the present invention may also be in the form of stand alone units. Typically, the deodorant containers filled with the perfumed stable gels can be used in conjunction with dispensers manufactured by the following: (1) F-Matic, (2) Impact, (3) Georgia Pacific, and (4) Technical Concepts. However, the container retaining the perfumed stable gel composition of the present invention is not limited to use with these dispensers.

One aspect of the present invention is to provide a disposable deodorant container adapted for supporting an air freshening deodorant in the form of a perfumed stable gel and adapted for placement in a dispenser, i.e., a battery operated fan dispenser unit, a stand alone unit, etc.

Another aspect of the present invention is to provide a disposable deodorant container which retains an improved perfumed stable gel composition that can be maintained as a gel when exposed to temperatures of from about 125° F. to about 150° F. and that has a perfume content of from about 70.0% to about 85.0% by weight of the composition. Another aspect of the present invention is to provide a disposable deodorant container which retains an improved perfumed stable gel which has both a long and uniform shelf life, and a long use or block life, while still maintaining an effective perfume content to deodorize over the life of the product.

Another aspect of the present invention is to provide a deodorant container having a simple design, compact size, considerable durability, and extensive adaptability to various deodorant dispensers.

Another aspect of the present invention is to provide a simple, economical process of manufacturing in unitary form a disposable deodorant container retaining an improved perfumed stable gel.

Other features and advantages of the invention will be apparent as set forth below and taken in conjunction with the following drawings.

BRIEF DESCRIPTION OF DRAWINGS

In the detailed description which follows, reference will be made to the following Figures, in which:

FIG. 1 shows a prior art container used to hold deodorant gels and the like;

FIG. 2 is a perspective view of the deodorant gel container of the present invention used with a typical stand alone dispenser unit;

FIG. 3 is a perspective view of the deodorant gel container of the present invention used with a typical battery operated fan dispenser unit;

DETAILED DESCRIPTION OF THE PREFERRED EMBODIMENT

This invention is susceptible of embodiments in many different forms. The drawings show and the specification describes in detail a preferred embodiment of the invention. It is to be understood that the present disclosure is to be considered as an exemplification of the principles of the invention. It is not intended to limit the broad aspects, of the invention to the illustrated embodiment.

Figures 1, 2, 3:
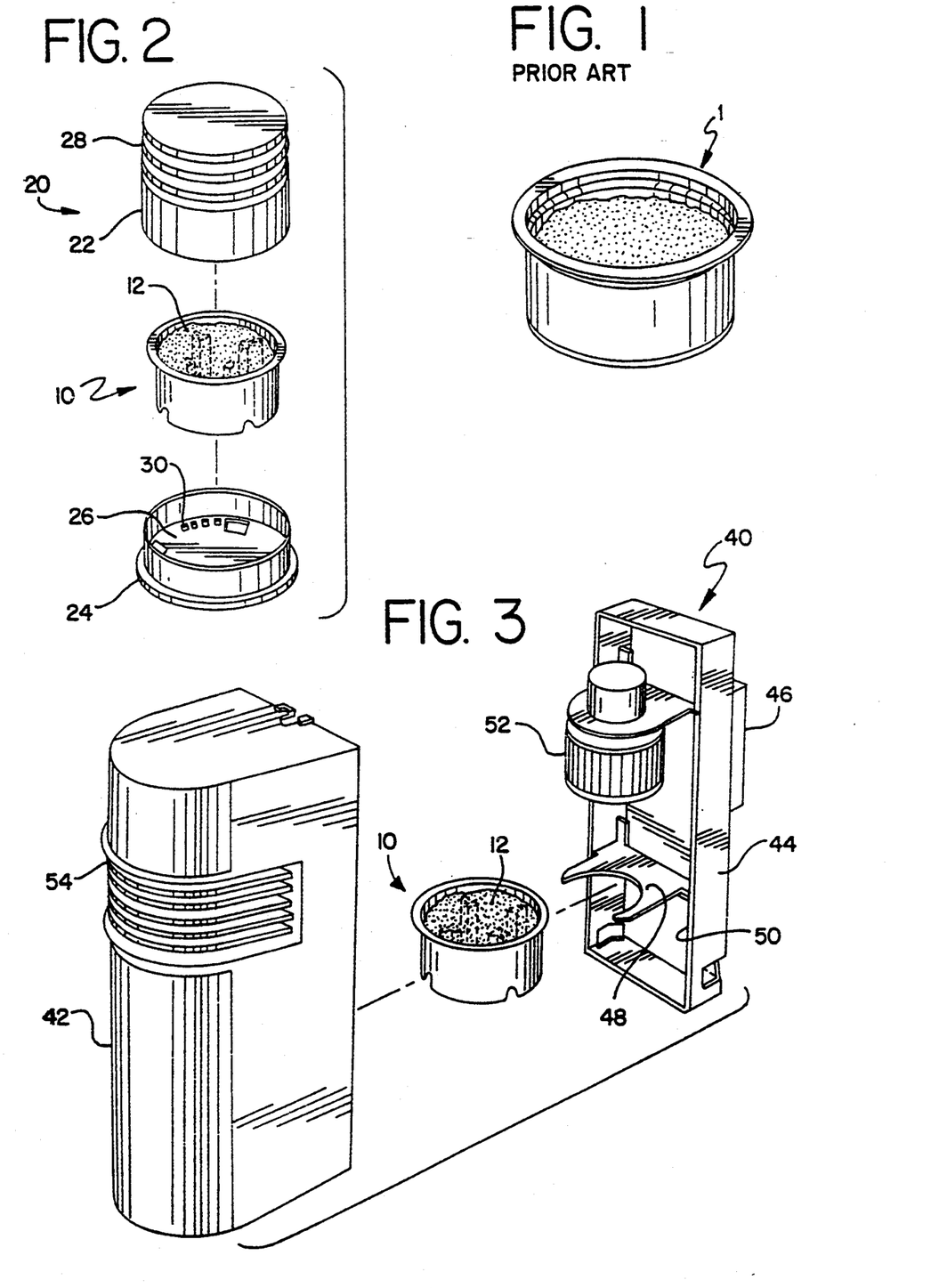

FIG. 1 shows a typical prior art container 1 used to hold a deodorant gel or the like.

FIG. 2 shows a deodorant container 10 of the present invention adapted for supporting an evaporative deodorant gel 12 in the form of a perfumed stable gel and adapted for placement in a typical stand alone dispenser unit 20. The container 10 is formed from a high density polyethylene. The stand alone dispenser unit 20 is typically placed on a table top, shelf or other substantially flat surface and comprises a lid portion 22 and a base portion 24. The lid portion 22 is adapted to fit easily and securely onto and over the base portion 24. The container 10 is adapted to fit onto the inner surface 26 of the base portion 24. Once the container 10 is securely placed onto the inner surface 26, the lid portion 22 is placed over the container 10 so as to conceal the container 10 from view. The lid portion 22 has lid vents 28 and the base portion 24 has base vents 30 so that the deodorant gel 12 can penetrate the air outside of the dispenser 20 while at the same time being concealed from view.

FIG. 3 shows the deodorant container 10 of the present invention adapted for supporting an evaporative deodorant gel 12 in the form of a perfumed stable gel and adapted for placement in a typical battery operated fan dispenser unit 40. The battery operated fan dispenser unit 40 is typically mounted on the wall of a room to be deodorized, i.e., a restroom. The fan dispenser unit 40 comprises a front cover portion 42 and a back portion 44. The back portion 44 has an attachment portion 46 which may have an adhesive on it for mounting the fan dispenser unit 40 to a wall or surface. The cover portion 42 is adapted to fit easily and securely against and over the back portion 44. The container 10 is adapted to fit into a holder portion 48 connected to an inner side 50 of the back portion 44. Once the container 10 is securely placed into the holder portion 48, the cover portion 42 is placed over the container 10 so as to conceal the container 10 from view. The fan dispenser unit 40 is typically powered by an energy source, such as a battery. When the fan dispenser unit 40 is turned on, the fan portion 52 located above the holder portion 48 acts to increase the rate at which the deodorant gel 12 is released into the air. As the deodorant gel 12 evaporates, the deodorant scent is released into the air of the room through cover vents 54.

Figure 4:
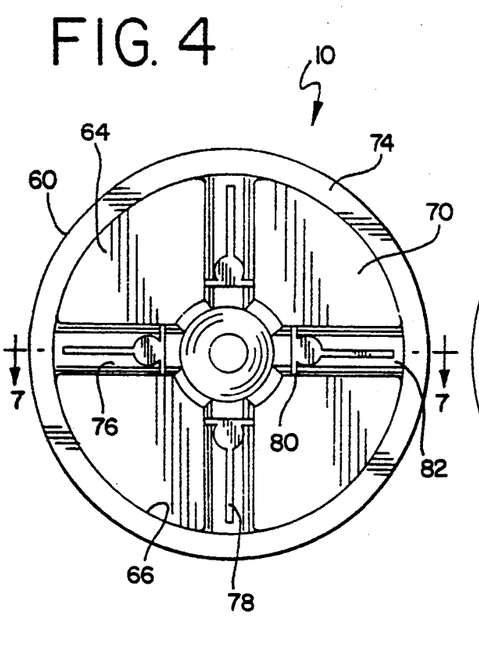
FIG. 4 is a top view of the deodorant container of the present invention.

FIG. 4 is a top view of the container 10 of the present invention. The container 10 comprises a generally cylindrical shaped shell 60 having a peripheral wall 62 (FIG. 6) and a base 64. The peripheral wall 62 has an inner side 66 and an outer side 68, and the peripheral wall 62 is about 3 cm (centimeters) in height. The base 64 has top surface 70 and a bottom surface 72, and the base 64 is about 6 cm in diameter. The peripheral wall 62 terminates with a radially outwardly extending lip 74, which supports the container 10 in a dispenser, i.e., on the holder portion 48 of fan dispenser unit 40 (FIG. 3).

On the top surface 70 of base 64 are a pair of intersecting diametrical ridges Four equi-angularly spaced support ribs 78 or fins extend upwardly from the ridges 76 and extend radially inwardly from the inner side 66 of peripheral wall 62. Each of the ribs 78 or fins terminates with a perpendicular end portion 80 toward the center of the container 10, and each of the four ribs 78 is spaced 90 degrees apart. The ribs 78 and the end portions 80 terminate about 0.2 cm below the lip 74. The ends of the ribs 78 closest to the inner side 66 of the peripheral wall 62 are not connected to the inner side 66 of the peripheral wall 62 but are spaced about 2 cm from the inner side 66 of the peripheral wall 62. Thus, a space 82 is formed between the inner side 66 of peripheral wall 62 and one end of rib 78.

Deodorant gels tend to shrink and harden as they evaporate. The ribs 78 and respective end portions 80 advantageously operate to reduce the rate of such shrinkage and hardening of the gel because the configuration of the ribs 78 and respective end portions 80 allows the perfumed stable gel 12 to spread uniformly throughout the container 10 when it is poured into the container and provides a greater surface area for the gel to spread over. A greater surface area allows for a more steady and uniform rate of evaporation of the gel and less collapse of the gel matrix. In contrast, when there is a reduction in the surface area over which the gel can spread, there is a greater reduction in the rate of fragrance release. In addition, when there is a greater surface area for liquid gel to spread over, the liquid gel crystals can solidify over a greater area and evenly cool and solidify at a faster rate.

In certain applications, such as on the inside surface of a cover for a diaper hamper, the container 10 is placed upside-down in a typical dispenser unit and with the air-exposed side of the gel facing downward. In these applications, the ribs 78 and respective end portions 80 advantageously operate to keep the deodorant gel 12 from falling downwardly out of the container 10.

Figure 5:
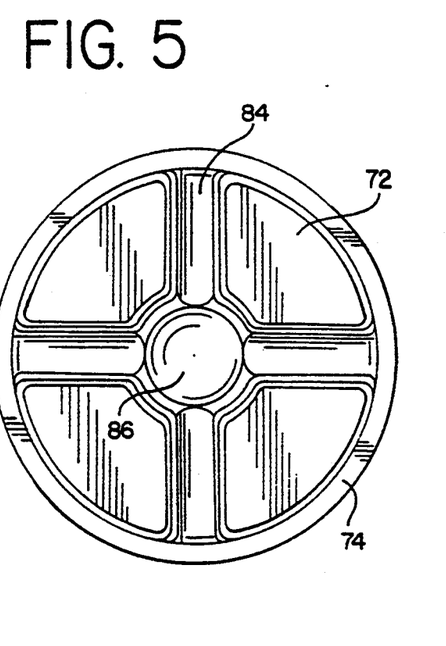
FIG. 5 is a bottom view of the deodorant container of the present invention.

FIG. 5 shows a bottom view of the container 10 of the present invention. The intersecting diametrical ridges 76 form corresponding intersecting diametrical grooves 84 on the bottom surface 72 of the base 64. The ribs 78 are aligned above the grooves 84. The grooves 84 intersect at 90 degree right angles at a circular portion forming a cavity 86. The grooves 84 are about 0.7 cm wide. The circular portion forming a cavity 86 is about 2 cm in diameter. These dimensions have been found to permit the container 10 to fit into most commercially available dispensers.

Figure 6:
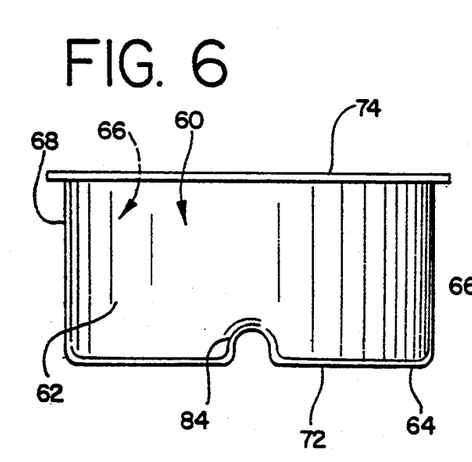
FIG. 6 is a side view of the deodorant container of the present invention.

FIG. 6 shows a side view of the container 10 with its generally cylindrical shell 60 and radially outwardly extending lip 74. The groove 84 is formed upwardly from the bottom surface 72 of the base 64 and is continuous with the outer side 68 of the peripheral wall 62.

Figure 7:
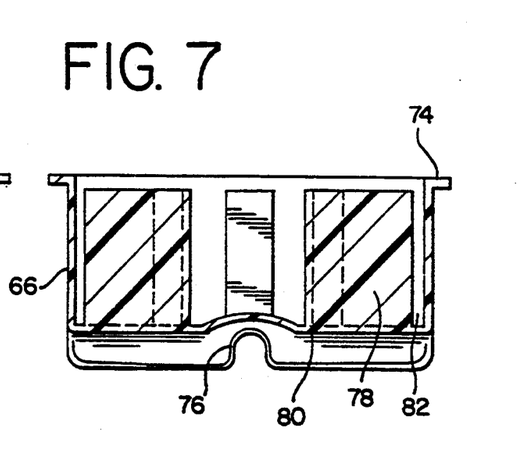
FIG. 7 is a cross-sectional view of the deodorant container of the present invention taken along line 7—7 of FIG. 4; and, FIGS. 8–12 show the test results for the rates of evaporation for various perfumed stable gels of the present invention.
Figure 8:
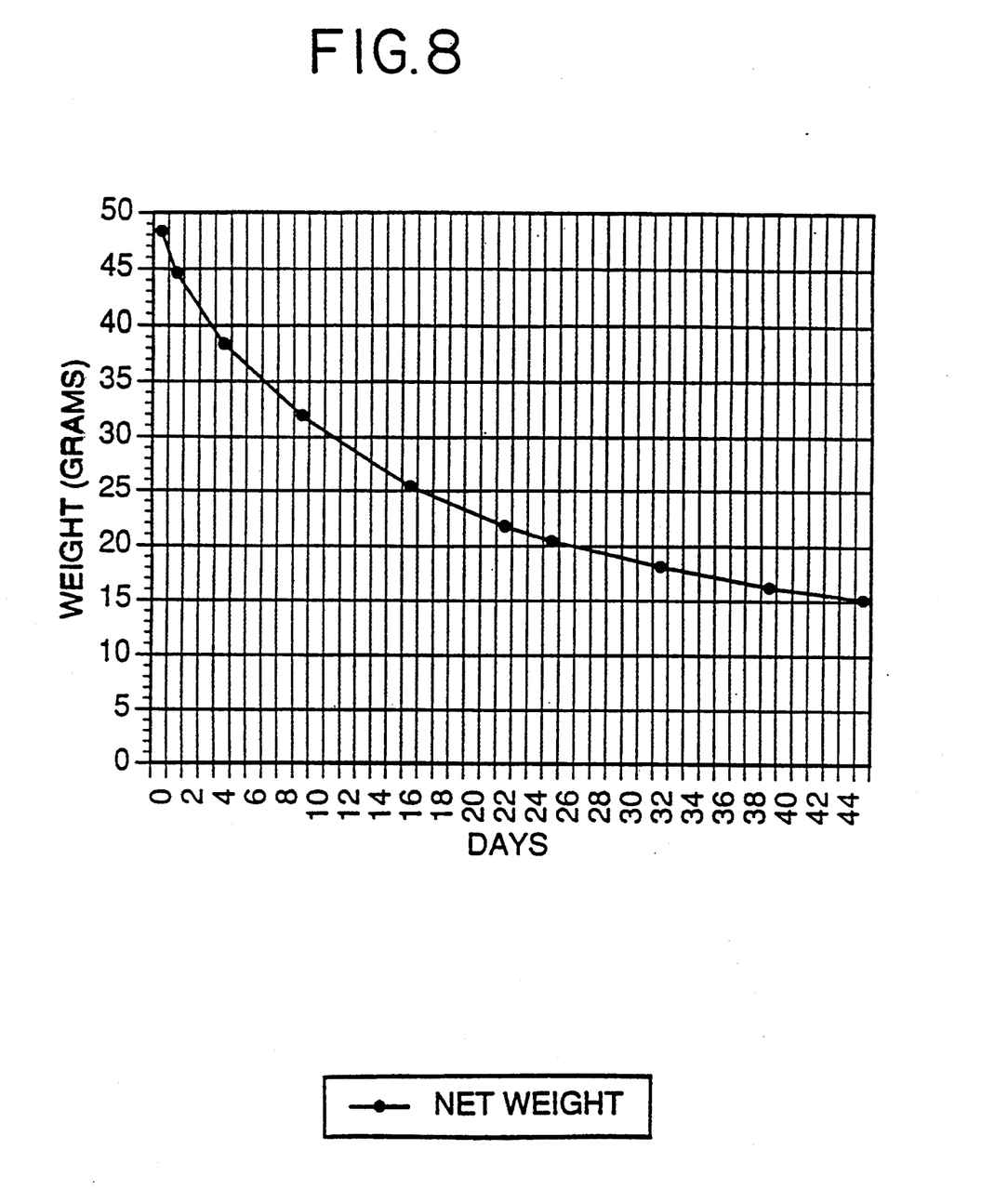
Figure 9:
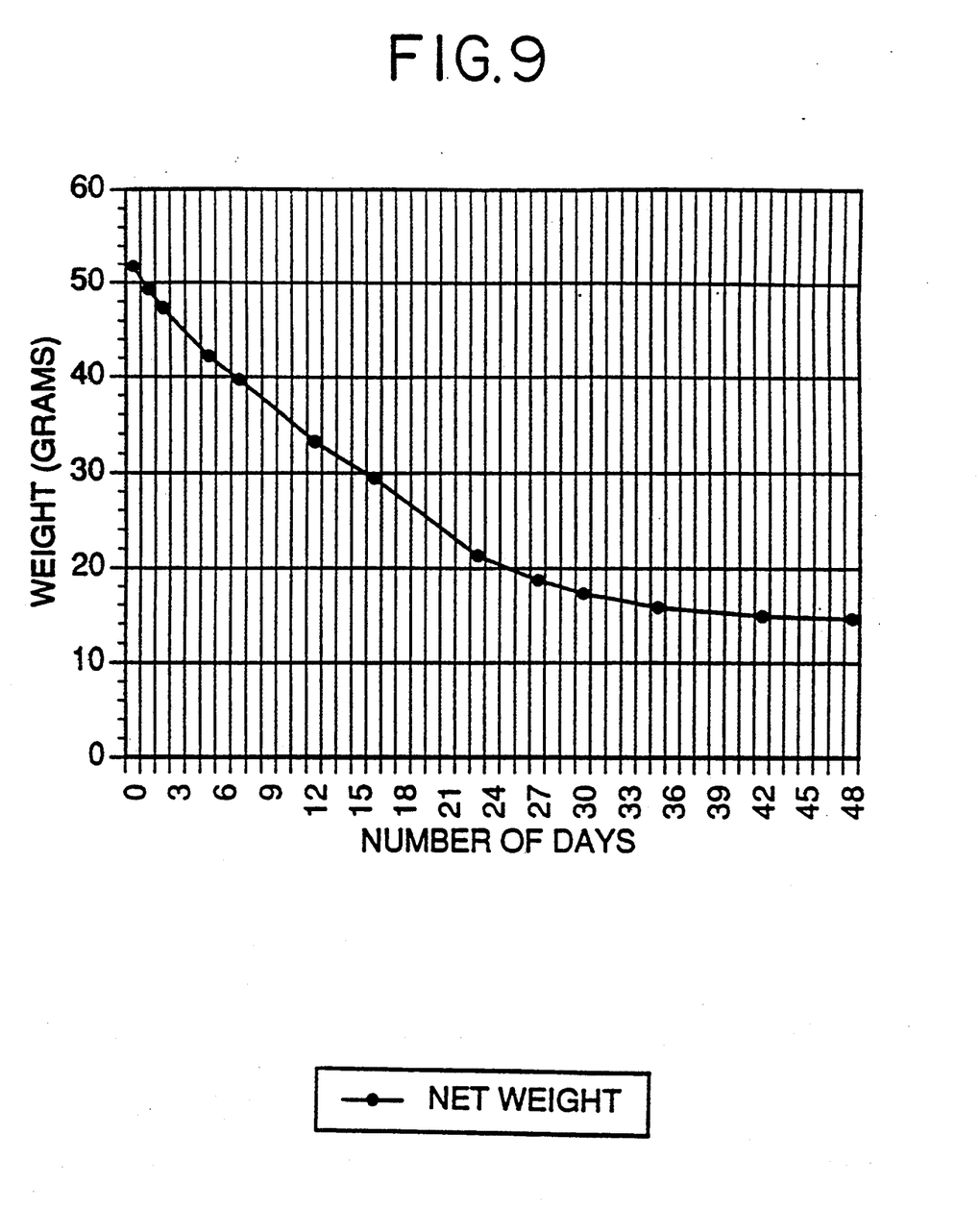
Figure 10:
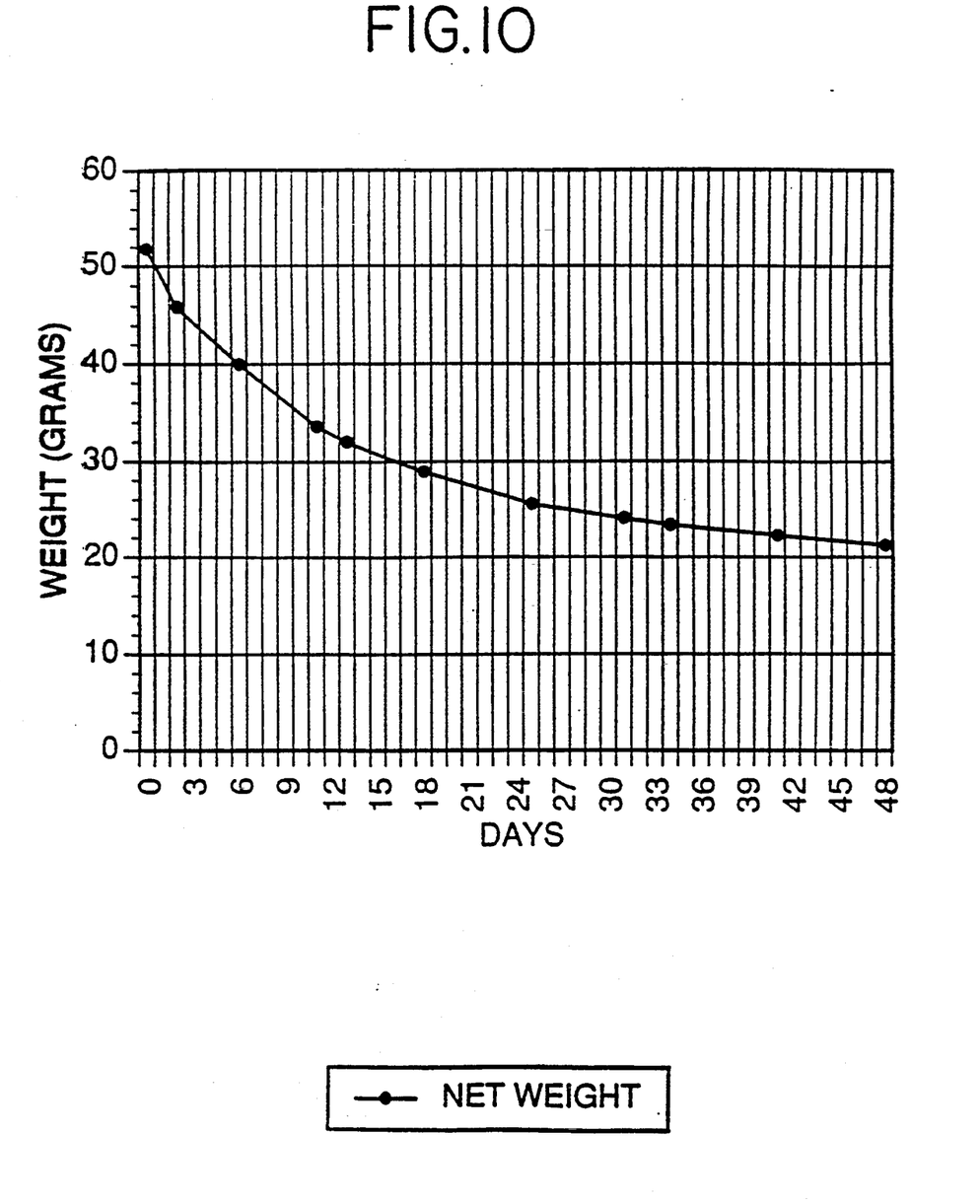
Figure 11:
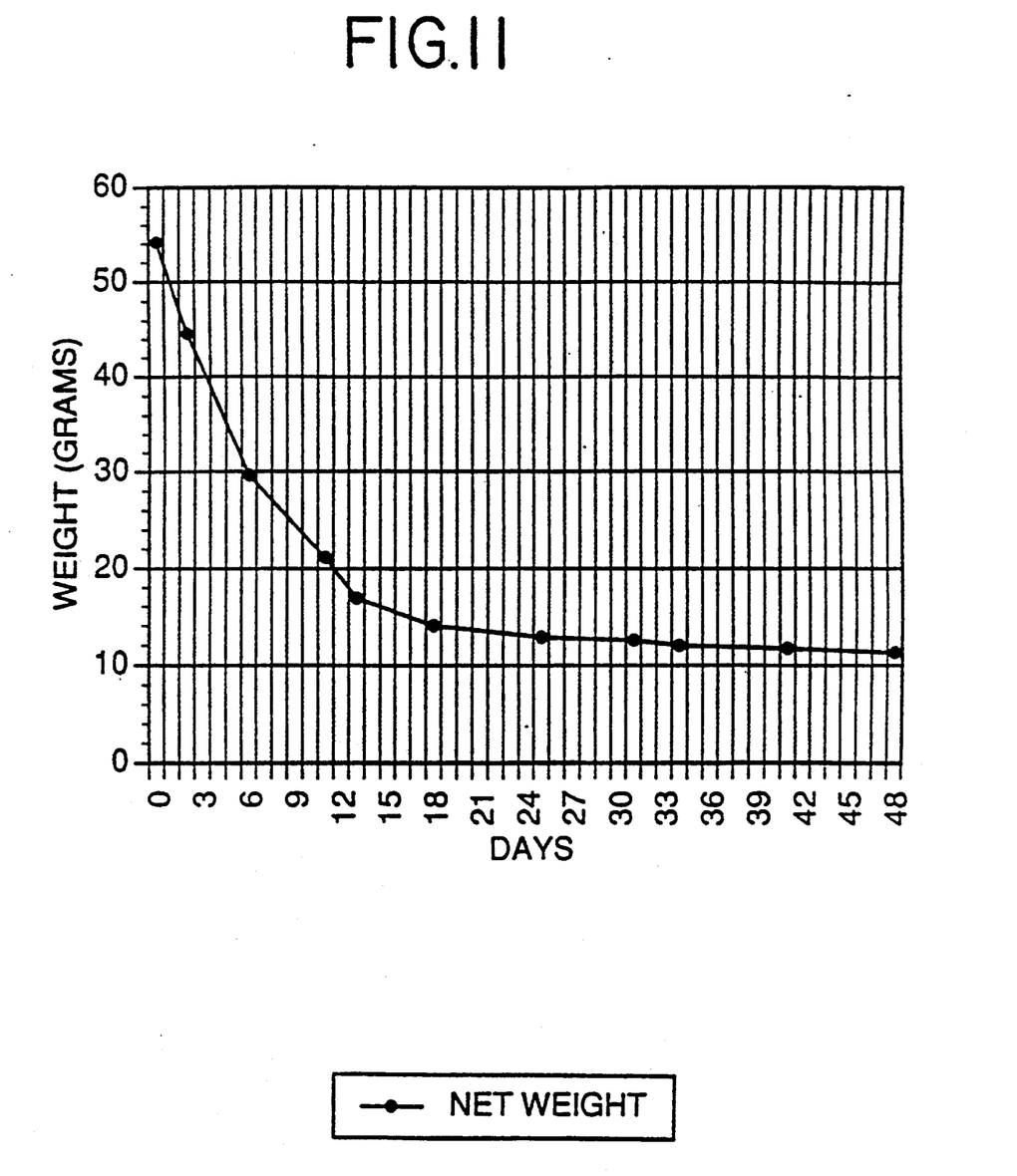
Figure 12:
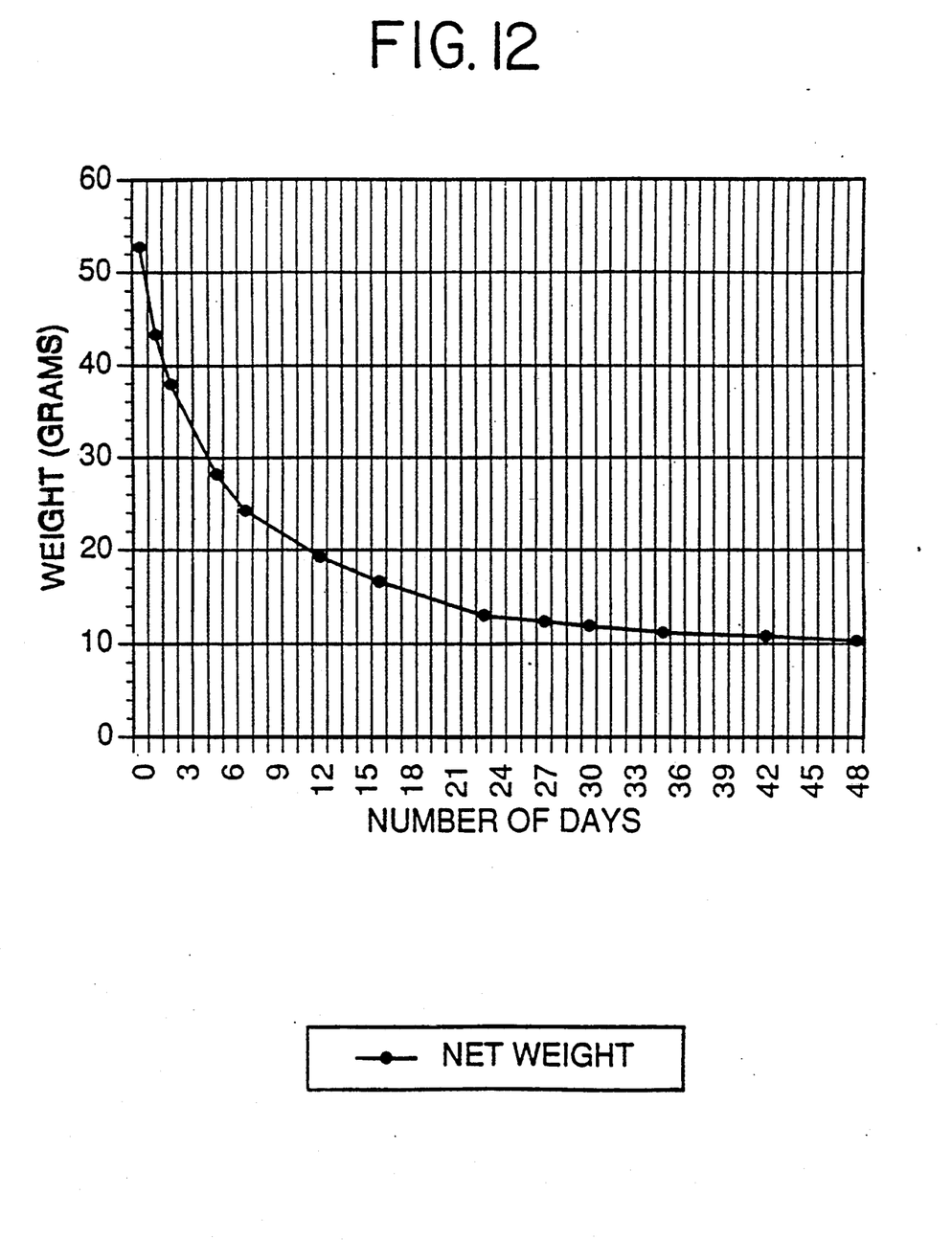

FIG. 7 is a cross-sectional view of the container 10 of the present invention taken along the line 7—7 of FIG. 4. Ribs 78 and respective end portions 80 are shaded.

When the deodorant gel 12 is originally packaged in the container 10, the gel 12 is covered with a protective heat-seal, such as foil, to prevent undesired evaporation. The foil may be removed when the container 10 is placed for use in typical dispenser units 20, 40.

In manufacturing the disposable deodorant container 10 of the present invention, injection molds are used in forming the containers. The first step involved in the manufacture of these plastic containers is the heating of the plastic to its melting point. The typical plastics used to form the containers of this invention include both high and low density polyethylenes. Once the plastic is melted, it is transferred through a barrel to be pressed. The plastic is then transferred into an injection mold to form the container, and once the container is formed, it is released from the mold. There is cool water circulating throughout the molds which acts to cool the plastic containers as they are formed. Approximately three to four containers can be made per minute with this process of manufacture. However, the cycle time for container formation varies depending on the type of plastic used.

The disposable deodorant container may retain a perfumed stable gel comprised of a unique combination of chemical components. The perfumed stable gel has a melting point temperature range of from about 125° F. to about 150° F. The preferred melting point temperature of the gel is about 140° F. The perfumed stable gel has a perfume content of from about 70.0% to about 85.0% by weight of the composition. The preferred perfume content is about 75.0% to about 80.0% by weight of the composition. The more preferred perfume content is about 75.0% by weight of the composition. Previously, it was difficult to manufacture a product that could be maintained as a stable gel when exposed to temperatures of from about 125° F. and about 150° F. at a perfume level of from about 70.0% to about 85.0% by weight of the composition. Obtaining a stable gel with a perfume content of from about 70.0% to about 85.0% by weight of the composition has also been difficult to develop from a solubility perspective as most other gels will liquefy, even at room temperatures, at levels of 50% perfume content. No one, to the inventors' knowledge, has been able to produce a stable gel with a melting point of from about 125° F. to about 150° F. and having a perfume content of from about 70.0% to about 85.0% by weight of the composition. The stable nature of the perfumed gel of the present invention means that the gel can be maintained as a solid, homogeneous, uniform mixture at temperatures from about 125° F. to about 150° F. and with a high perfume content of from about 70.0% to about 85.0% by weight of the composition. The perfumed stable gel will not liquefy or form a slurry, but will remain as a solid, under the above temperature conditions and having the above perfume content.

All percentages of ingredients or phases given herein are weight percentages of the entire perfumed stable gel composition, unless otherwise indicated.

The perfumed stable gel composition of the present invention includes water in an amount of from about 2.0% to about 10.0% by weight of the composition. Preferably, the water is at its boiling point when initially mixed with an odorless glycol, and preferably the water is in an amount of about 5.0% by weight of the composition.

The perfumed stable gel composition also includes a soap in an amount of from about 5.0% to about 15.0% by weight of the composition. The preferred soap is sodium stearate having a carbon content in the range of $C_{12}$–$C_{20}$ and having a melting point of about 158° F. or higher. Preferably, the soap is in an amount of about 7.5% by weight of the composition in the formulations for the cherry, jasmine, baby powder, and spice deodorant gels. Preferably, the soap is in an amount of about 9.0% by weight of the composition in the formulations for the green apple, lemon, bubble gum, spearmint, and gardenia deodorant gels. The increased amount of soap in these latter formulations increases the melting point and aids in solubilizing the perfumes.

The perfumed stable gel composition also includes a non-ionic surfactant. The use of a non-ionic surfactant in the composition of the present invention helps to increase the melting point of the composition and aids in initially maintaining the composition product in solution and later stabilizing the composition product as a solid. Preferably, the non-ionic surfactant contains a sufficient amount of ethylene oxide to provide a melting point temperature in the range of from about 100° F. to about 150° F. The non-ionic surfactant is preferably in an amount of from about 2.0% to about 15.0% by weight of the composition. More preferably, the non-ionic surfactant is in an amount of about 3.75% by weight of the composition. The preferred non-ionic surfactants that are used in the present invention include nonylphenols, polyethylene glycols, or a mixture thereof. The nonylphenols may include Nonoxynol 100, with 100 mols of ethylene oxide in the product, Iconol NP-100, and nonylphenols of 80 mols up to 150 mols. The polyethylene glycols may include polyethylene glycol 8000 and BASF's Pluracol line. Other non-ionic surfactants that can be used include non-ionics similar to BASF's Tetronic and Tetronic R line. However, this latter group of non-ionic surfactants is currently more expensive to use than the former groups.

The perfumed stable gel composition also includes a preservative in an amount of from about 0.1% to about 0.3% by weight of the composition. The preservative helps to inhibit the growth of mold or fungus on the surface of the perfumed stable gel. The preferred preservative used in the present invention is Glydant (chemically known as DMDM Hydantoin (55% solution)($C_7H_{12}N_2O_4$)—Chemical Abstract No. is 6440-58-0). Preferably, the preservative is in an amount of about 0.25% by weight of the composition.

The perfumed stable gel composition may also include a perfume component. It has been found that an effective perfume content for the composition of the present invention is in an amount of from about 70.0% to about 85.0% by weight of the composition. The preferred amount of perfume is about 75.0% to about 80.0% by weight of the composition. The more preferred amount of perfume is about 75.0% by weight of the composition. The perfume agent enhances the odor characteristics of the product. Specific examples of suitable perfume agents include lemon, bubble gum, cherry, spearmint, green apple, baby powder, gardenia, jasmine, herbal, spice, and others. The primary scents used are obtained from the fruity and floral scent groups. However, it is possible to produce any number of different scents depending on the type of scent desired.

The perfumed stable gel composition also includes an odorless glycol. The amount of odorless glycol used in the chemical composition should be sufficient to aid in solubilizing the perfume component. It has been found that the addition of an odorless glycol aids in the stability of the evaporation rate of the composition and aids in increasing the melting point of the composition. Preferably, the amount of odorless glycol used is in an amount of from about 0.1% to about 12.0% by weight of the composition. The preferred amount of odorless glycol is about 8.75% by weight of the composition. The preferred odorless glycols used in the composition include propylene glycol, glycerol, hexylene glycol, or a mixture of two or more thereof.

The perfumed stable gel composition may also include a color dye which acts to enhance the physical appearance of the product and color code the product. The preferred amount of dye used is from 0% to about 0.01% by weight of the composition. Since some of the perfumes used in the composition of the present invention have a natural color inherent in the perfume, it may not be necessary to add a dye to the composition when such perfumes are used, as the perfumes impart their color to the perfumed stable gel. Heat stable dyes are preferred for use in the composition. The most preferred dyes used in the composition, alone or in combination, include Yellow #5, F,D & C (Food, Drug a Cosmetic) #1 Blue, Rhodamine B (a reddish-pink dye)

and Pylaklor Orange (Pylaklor is the trade name associated with the Pylam Company).

The perfumed stable gel composition may also include inert filler materials. The amount of filler material used in the composition is from 0% to about 4.0% by weight of the composition. Preferably, the amount of filler material used is about 0.5% by weight of the composition. The filler material may be selected from the group including diatemaceous earth, clay, dirt, silica and sand. The addition of these filler materials to the composition is optional. However, the filler material helps to control the evaporation rate of the perfume component.

The perfumed stable gel composition may also include ethanol or odorless mineral spirits. The amount of ethanol or odorless mineral spirits used is from 0% to about 5.0% by weight of the composition. Preferably, the amount of ethanol or odorless mineral spirits used is about 3.0% by weight of the composition. The ethanol and odorless mineral spirits aid in solubilizing some of the perfumes and in lowering the costs of manufacturing some of the more expensive perfumes (i.e., green apple) without affecting the performance of the gels. Preferably, the mineral spirits are comprised of aliphatic hydrocarbons.

The manufacture of the perfumed stable gel involves the mixing of: (1) an oil phase and (2) a water phase. The oil phase includes the non-ionic surfactant and the desired perfume. First, the non-ionic surfactant is heated to a temperature in the range of from about 120° F. to about 150° F. It is heated in a 55 gallon jacketed stainless steel mixing vessel. Heating bands surrounding the mixing vessel act to heat and liquefy the non-ionic surfactant. The non-ionic surfactant is heated in this manner for about 24 to 48 hours, depending on the size of the batch and the heating temperatures used.

After the non-ionic surfactant has been sufficiently heated and liquefied, it is transferred to a smaller open-top 55 gallon jacketed stainless steel mixing vessel. This mixing vessel also has heating bands surrounding it which act to heat the non-ionic surfactant and the perfume, which is added at this step in a pre-measured amount. The two components are thoroughly mixed in the mixing vessel with an electric mixer that has an attached agitator working at approximately 750 rpm. The perfume is mixed with the non-ionic surfactant for approximately 10 minutes at a temperature in the range of about 120° F. to about 150° F.

The second phase involved in forming the perfumed stable gel is the water phase. To manufacture the water phase, a pre-measured amount of the odorless glycol is added to boiling hot water. The glycol and water are mixed together in an open-top 55 gallon jacketed stainless steel mixing vessel. The two components are thoroughly mixed in the mixing vessel with an electric mixer that has an attached agitator working at approximately 750 rpm. The odorless glycol is mixed into the hot water for approximately 5 minutes at a temperature of about 158° F. Next, the soap is added in a pre-measured amount to the glycol/water mixture. The soap is thoroughly mixed into the glycol/water mixture in the mixing vessel until the soap is dissolved and there are no clumps remaining. The soap is mixed with the odorless glycol and water for approximately 15 minutes to 30 minutes at a temperature of about 158° F.

Next, the mixture of the water, the odorless glycol, and soap, i.e., the water phase, is added to the non-ionic surfactant and perfume, i.e., the oil phase. All of these components are thoroughly blended at a temperature of over 140° F. in the mixing vessel with an electric mixer that has an attached agitator working at approximately 750 rpm. The preservative is added at this stage of the mixing. The dye can be added to the mixture at this stage or it can be added previously in the water phase mixture. All of these components are then thoroughly mixed for approximately 15 minutes.

Finally, an optional filler material dan be added to the mixture by spooning with a ladle, a desired amount of the filler material into the mixture. The mixture is stirred thoroughly until the desired consistency is reached.

Once it is determined that the composition is thoroughly blended and while it is still in the molten state, the composition is spooned with a ladle out of the mixing vessel and into the individual deodorant containers.

Lastly, the containers holding the composition are cooled by placing the dispensers on a conveyer belt and blowing cold air upon those dispensers. The cold air is passed through a tunnel fed by an air conditioning unit. During the containers' 3 to 5 minutes in the tunnel, the gel composition solidifies in the dispenser assembly, thus securing the completed perfumed stable gel in the disposable deodorant container. The amount of composition prepared at one time is limited to the amount that is to be filled in the dispensers on a particular day. Typically, this amount can vary between 200 pounds to 400 pounds per day. The following Example 1 illustrates the preparation of a preferred perfumed stable gel composition. Test results for the rates of evaporation of various perfumed stable gels are shown in FIGS. 8–12 and the corresponding recorded weights of the various gels during the evaporation period are shown in Tables 1–5. Also, formulations for various perfumed stable gel compositions are shown in Table 6.

EXAMPLE I

A preferred perfumed stable gel of the present invention was prepared as described below, having a cherry perfume and having the composition shown below.

| COMPONENT | PERCENT BY WEIGHT OF COMPOSITION |
|---|---|
| Water | 5.00% |
| Propylene Glycol | 8.75% |
| Sodium Stearate | 7.50% |
| Perfume | 74.75% |
| ICONOL NP 100 | 3.75% |
| Glydant | 0.24% |
| Dye | 0.01% |

The amount of composition prepared at one time is limited to the amount that is to be filled in the deodorant containers on a particular day. In the manufacture of the perfumed stable gel retained in the disposable dispenser, there are two distinct phases involved: (1) the oil phase and (2) the water phase. The oil phase involves mixing the non-ionic surfactant with the desired perfume. First, the iconol NP 100 is heated to a temperature in the range of from about 120° F. to about 150° F. The Iconol is heated in a 55 gallon jacketed stainless steel mixing vessel with surrounding heating bands that act to heat and liquefy the Iconol. The Iconol is heated in this manner for about 24 to about 48 hours, depending on the size of the batch and the heating temperatures used.

After the Iconol has been sufficiently heated and liquefied, it is transferred to an open-top 55 gallon jacketed stainless steel mixing vessel. This mixing vessel also has heating bands surrounding it which act to heat the non-ionic surfactant and the perfume, which is added at this step in a pre-measured amount. The two components are thoroughly mixed in the mixing vessel with an electric mixer having an attached agitator working at approximately 750 rpm. The perfume is mixed with the Iconol for approximately 10 minutes at a temperature in the range of about 120° F. to about 150° F.

The second phase in the formation of the perfumed stable gel is the water phase. In this phase a pre-measured amount of the propylene glycol is added to boiling hot water and mixed together in an open-top 55 gallon jacketed stainless steel mixing vessel. The propylene glycol and water are thoroughly mixed in the mixing vessel with an electric mixer that has an attached agitator working at approximately 750 rpm. The propylene glycol is mixed with the hot water for approximately 5 minutes at a temperature of about 158° F. Next, the sodium stearate soap is added in a pre-measured amount to the propylene glycol/water mixture. The sodium stearate is thoroughly mixed with the propylene glycol and water in the mixing vessel until the sodium stearate is dissolved and there are no clumps. The sodium stearate is mixed with the propylene glycol and water for approximately 15 to 30 minutes at a temperature of about 158° F.

Next, the mixture of water, propylene glycol, and sodium stearate, i.e., the water phase, is added to the mixture of Iconol and perfume, i.e., the oil phase. The components from the oil phase and the water phase are thoroughly blended at a temperature of over 140° F. in the mixing vessel with an electric mixer that has an attached agitator working at approximately 750 rpm. The preservative is added at this stage of mixing. The dye can be added to the mixture at this stage or it may have been previously added to the water phase mixture. These components are then thoroughly mixed for approximately 15 minutes.

Optionally, filler material may be added to the mixture. This is done by spooning with a ladle, a desired amount of the filler material into the mixture. The mixture is then thoroughly stirred until the desired consistency is reached.

When the composition has been thoroughly blended, and while still in the molten state, the composition is spooned with a ladle out of the mixing vessel and into the individual deodorant containers.

Lastly, the containers holding the composition are cooled by placing the dispensers on a conveyer belt and blowing cold air upon those dispensers. The cold air is passed through a tunnel fed by an air conditioning unit. The containers are placed on a conveyer belt and cooled in the tunnel for about 3 to 5 minutes, and the gel composition solidifies in the dispenser assembly, thus securing the completed perfumed stable gel in the disposable deodorant container. The amount of composition prepared at one time is limited to the amount that is to be filled in the dispensers on a particular day. Typically, this amount can vary between 200 pounds to 400 pounds per day.

Tests were also conducted to determine the evaporation rates of various perfumed stable gels. The test results recording the rates of evaporation for various perfumed stable gels are shown in the accompanying FIGS. 8–12 (FIG. 8—Spearmint, FIG. 9—Jasmine, FIG. 10—Gardenia, FIG. 11—Cherry, FIG. 12—Bubble Gum). In conducting these tests, although samples of the perfumed stable gels were made in the lab in smaller amounts than usual and the components were mixed together in smaller mixing vessels and heated on hot plates, the other procedures used in making the gels were the same as those described above. After the gels were made, they were weighed, less the weight of the plastic deodorant containers. The gels were then placed in the plastic deodorant containers, and the containers were placed in battery operated fan units located in various offices, bathrooms and closets around the production building. All of the rooms were maintained at room temperature throughout the experiment. The fans were turned on at the start of the experiment and operated continuously for 24 hours per day throughout the testing period. In every day operation and normal use, fans would probably not be operated for a continuous 24 hour period, and different types of battery operated fan units could be used with the deodorant gels. For example, sophisticated battery units are available that either have an infrared motion detector or a light sensitive eye that turns the machines on and off. These types of units cause the fan to operate for only a portion of the time as opposed to the continuous operation in the experiments conducted herein.

The weights of the gels were then recorded at various intervals as indicated by the black dots on the graphs. The average gel system evaporated at a rate sufficient to allow the product to last up to 45 days when used at room temperature with a battery operated fan unit which was continuously running. Thus, the gels are capable of lasting for even a longer period of time with less exposure under a fan.

In addition, the formulations for various perfumed stable gel compositions that were prepared are shown in Table 6.

It will be understood that the invention may be embodied in other specific forms by one of ordinary skill in the art without departing from its spirit or central characteristics. The present example and embodiment is thus to be considered as illustrative and not restrictive, and the invention is not intended to be limited to the details of the listed embodiments. Rather, the invention is defined by the claims, and as broadly as the prior art will permit.

What we claim is:

1. A perfumed stable gel composition comprising:
   water in an amount of from about 2.0% to about 10.0% by weight of said composition;
   a soap in an amount of from about 5.0% to about 15.0% by weight of said composition;
   a non-ionic surfactant in an amount of from about 2.0% to about 15.0% by weight of said composition;
   a preservative in an amount of from about 0.1% to about 0.3% by weight of said composition;
   an odorless glycol in an amount of from about 0.1% to about 12% by weight of said composition; and,
   a perfume in an amount of from about 70.0% to about 85.0% by weight of said composition,
   wherein said gel composition is capable of being maintained as a stable gel at a temperature of from about 125° F. to about 150° F.

2. The perfumed stable gel composition of claim 1 further comprising a heat stable dye in an amount of about 0.01% or less by weight of said composition.

3. The perfumed stable gel composition of claim 1 further comprising a filler material in an amount of about 4.0% or less by weight of said composition.

4. The perfumed stable gel composition of claim 3 wherein said filler material is selected from the group consisting of diatemaceous earth, clay, dirt, silica and sand.

5. The perfumed stable gel composition of claim 1 further comprising ethanol in an amount of about 5.0% or less by weight of said composition.

6. The perfumed stable gel composition of claim 1 further comprising odorless mineral spirits in an amount of about 5.0% or less by weight of said composition.

7. The perfumed stable gel composition of claim 6 wherein said odorless mineral spirits are aliphatic hydrocarbons.

8. The perfumed stable gel composition of claim 1 wherein said water is in an amount of about 5.0% by weight of said composition.

9. The perfumed stable gel composition of claim 1 wherein said soap is in an amount of about 7.5% by weight of said composition.

10. The perfumed stable gel composition of claim 1 wherein said soap is sodium stearate.

11. The perfumed stable gel composition of claim 1 wherein said non-ionic surfactant is in an amount of about 3.75% by weight of said composition.

12. The perfumed stable gel composition of claim 1 wherein said non-ionic surfactant is selected from the group consisting of a nonylphenol, a polyethylene glycol, and a mixture thereof.

13. The perfumed stable gel composition of claim 1 wherein said preservative is in an amount of about 0.25% by weight of said composition.

14. The perfumed stable gel composition of claim 1 wherein said odorless glycol is in an amount of about 8.75% by weight of said composition.

15. The perfumed stable gel composition of claim 1 wherein said odorless glycol is selected from the group consisting of a propylene glycol, a glycerol, a hexylene glycol, and a mixture thereof.

16. The perfumed stable gel composition of claim 1 wherein said perfume is in an amount of about 75.0% by weight of said composition.

17. The perfumed stable gel composition of claim 1 wherein said perfume is selected from the group consisting of lemon, bubble gum, cherry, spearmint, jasmine, green apple, baby powder, spice and gardenia.

18. A perfumed stable gel composition comprising:
water in an amount of from about 2.0% to about 10.0% by weight of said composition;
sodium stearate in an amount of from about 7.0% to about 15.0% by weight of said composition;
a non-ionic surfactant selected from the group consisting of a nonylphenol, a polyethylene glycol, and a mixture thereof, in an amount of from about 2.0% to about 15.0% by weight of said composition;
a perfume selected from the group consisting of lemon, bubble gum, cherry, spearmint, jasmine, green apple, baby powder, spice, and gardenia, in an amount of from about 70.0% to about 85.0% by weight of said composition;
a preservative in an amount of from about 0.1% to about 0.3% by weight of said composition; and,
an odorless glycol selected from the group consisting of a propylene glycol, a glycerol, a hexylene glycol, and a mixture thereof, in an amount of from about 0.1% to about 12.0% by weight of said composition;
wherein said gel composition is capable of being maintained as a stable gel at a temperature of from about 125° F. to about 150° F.

19. The perfumed stable gel composition of claim 18 further comprising a heat stable dye in an amount of about 0.01% or less by weight of said composition.

20. The perfumed stable gel composition of claim 18 further comprising ethanol in an amount of about 5.0% or less by weight of said composition.

21. The perfumed stable gel composition of claim 18 further comprising odorless mineral spirits in an amount of about 5.0% or less by weight of said composition.

22. The perfumed stable gel composition of claim 18 further comprising filler material selected from the group consisting of diatemaceous earth, clay, dirt and sand, in an amount of about 4.0% or less by weight of said composition.

23. The perfumed stable gel composition of claim 18 wherein said perfume content is in an amount of about 75.0% by weight of said composition.

24. The perfumed stable gel composition of claim 18 wherein said composition is maintained as a stable gel at a temperature of 140° F.

25. A perfumed stable gel composition comprising:
water in an amount of from about 2.0% to about 10.0% by weight of said composition;
sodium stearate in an amount from about 7.0% to about 15.0% by weight of said composition;
a non-ionic surfactant selected from the group consisting of a nonylphenol, a polyethylene glycol, and a mixture thereof, in an amount of from about 2.0% to about 15.0% by weight of said composition;
a perfume selected from the group consisting of lemon, bubble gum, cherry, spearmint, jasmine, green apple, baby powder, spice, and gardenia, in an amount of from about 75.0% to about 80.0% by weight of said composition;
a preservative in an amount of from about 0.1% to about 0.3% by weight of said composition;
an odorless glycol selected from the group consisting of a propylene glycol, a glycerol, a hexylene glycol, and a mixture thereof, in an amount of from about 1.0% to about 12.0% by weight of said composition, and;
a filler material selected from the group consisting of diatemaceous earth, clay, dirt and sand, in an amount of 4.0% or less by weight of said composition;
a heat stable dye in an amount of about 0.01% or less by weight of said composition; and,
ethanol or odorless mineral spirits in an amount of about 5.0% or less by weight of said composition;
wherein said gel composition is capable of being maintained as a stable gel at a temperature of from about 130° F. to about 150° F.

26. The perfumed stable gel composition of claim 25 wherein said perfume content is in an amount of about 75.0% by weight of said composition.

27. The perfumed stable gel composition of claim 25 wherein said composition is maintained as a stable gel at a temperature of 140° F.

28. A perfumed stable gel composition comprising:
2%–10% of water by weight of said composition;
5%–15% of sodium stearate by weight of said composition;

2%–15% of a non-ionic surfactant by weight of said composition;

0.1%–12% of an odorless glycol by weight of said composition;

0.1%–0.3% of a preservative by weight of said composition; and, 70.0%–85.0% of a perfume by weight of said composition, wherein said composition can be maintained at a temperature of between about 125° F. and about 150° F.

29. The perfumed stable gel composition of claim 28 further comprising 0.01% or less dye by weight of said composition.

30. The perfumed stable gel composition of claim 28 further comprising 4.0% or less of a filler material by weight of said composition.

31. The perfumed stable gel composition of claim 28 further comprising 5.0% or less of ethanol or odorless mineral spirits by weight of said composition.

32. The perfumed stable gel composition of claim 28 wherein said perfume is in an amount of about 75.0% by weight of said composition.

33. The perfumed stable gel composition of claim 28 wherein said composition is maintained as a stable gel at a temperature of 140° F.

* * * * *

UNITED STATES PATENT AND TRADEMARK OFFICE
CERTIFICATE OF CORRECTION

PATENT NO. : 5,419,879
DATED : May 30, 1995
INVENTOR(S) : Eftichios V. Vlahakis et al.

It is certified that error appears in the above-indentified patent and that said Letters Patent is hereby corrected as shown below:

Column 3, line 33, delete "1.25" and insert --125--.

Column 5, line 55, after "ridges" insert --76.--.

Column 10, line 9, delete "dan" and insert --can--.

Column 11, line 20, delete "water-for" and insert --water for--.

Signed and Sealed this

Fourteenth Day of November, 1995

Attest:

BRUCE LEHMAN

*Attesting Officer*   *Commissioner of Patents and Trademarks*